United States Patent
Larson et al.

(10) Patent No.: US 8,713,948 B2
(45) Date of Patent: May 6, 2014

(54) SYSTEMS, METHODS, AND DEVICES FOR FROZEN SAMPLE DISTRIBUTION

(71) Applicants: President and Fellows of Harvard College, Cambridge, MA (US); Northeastern University, Boston, MA (US)

(72) Inventors: Dale Larson, Waban, MA (US); Jeffrey Ruberti, Lexington, MA (US); John Slusarz, Hopedale, MA (US); Trevor Ehret, Syracuse, NY (US); Nicholas Goulas, Tewksbury, MA (US); Erin Rush, Middletown, CT (US)

(73) Assignees: President and Fellows of Harvard College, Cambridge, MA (US); Northeastern University, Boston, MA (US)

( * ) Notice: Subject to any disclaimer, the term of this patent is extended or adjusted under 35 U.S.C. 154(b) by 0 days.

(21) Appl. No.: 13/901,045

(22) Filed: May 23, 2013

(65) Prior Publication Data

US 2013/0333399 A1 Dec. 19, 2013

Related U.S. Application Data

(63) Continuation of application No. 12/087,695, filed as application No. PCT/US2007/001094 on Jan. 16, 2007, now Pat. No. 8,448,456.

(60) Provisional application No. 60/758,807, filed on Jan. 13, 2006.

(51) Int. Cl.
*F25D 25/00* (2006.01)

(52) U.S. Cl.
USPC ............................................ 62/62; 62/320

(58) Field of Classification Search
CPC . F25D 25/00; F25D 2303/081; F25D 19/006; F25C 5/0043–5/0046; G01R 33/3804
USPC ............. 62/62, 320, 341, 51.1; 600/567, 568; 435/30, 40.5
See application file for complete search history.

(56) References Cited

U.S. PATENT DOCUMENTS

| 6,582,967 B2 * | 6/2003 | Muraca | 436/174 |
| 8,278,034 B2 * | 10/2012 | Muraca | 422/68.1 |
| 2002/0106626 A1 * | 8/2002 | Muraca | 435/1.3 |
| 2005/0234336 A1 * | 10/2005 | Beckman et al. | 600/431 |

* cited by examiner

*Primary Examiner* — Mohammad M Ali
(74) *Attorney, Agent, or Firm* — Lawson & Weitzen, LLP; Sonia K. Guterman; Michael I. Falkoff

(57) ABSTRACT

A drilling system including a motor that produces a sonic, linear oscillatory motion is provided for removing a frozen biological sample from a stored frozen specimen and methods of use thereof without thawing the remainder of the specimen. The stator and slider assembly is operated by a servo controller which can communicate and be programmed through a port of a PC equipped with software.

24 Claims, 5 Drawing Sheets

SYSTEMS, METHODS, AND DEVICES FOR FROZEN SAMPLE DISTRIBUTION

RELATED APPLICATIONS

The present application claims the benefit of U.S. provisional patent application Ser. No. 60/758,807 filed Jan. 13, 2006, PCT application having serial number PCT/US07/01094, filed in the PCT Receiving Office of the U.S. Patent and Trademark Office Jan. 16, 2007, and U.S. national phase application Ser. No. 12/087,695, issue date May 28, 2013 as U.S. Pat. No. 8,448,456, each of which is hereby incorporated herein by reference in its entirety.

GOVERNMENT SUPPORT

This invention was made with government support under CA114167 awarded by the National Institutes of Health. The government has certain rights in the invention.

TECHNICAL FIELD

The present invention relates to a coring system for extracting frozen biological samples from frozen specimens without thawing the specimen, and methods of use thereof.

BACKGROUND

Stored biological samples in biorepositories are an important resource for research into the diagnosis and etiology of diseases. Biological specimens are stored in military facilities, forensic DNA banks, government laboratories, diagnostic pathology and cytology laboratories, commercial enterprises, and nonprofit organizations such as hospitals. Preservation and analysis of biological samples increases knowledge about diseases and provides a basis for developing better processes to prevent, diagnose, and treat these diseases.

A conservative estimate shows that 282 million specimens are currently stored in U.S. facilities, and the rate has been increasing at 20 million specimens per year beginning since 1998 (National Bioethics Advisory Commission, "Research Involving Human Biological Materials: Ethical Issues and Policy Guidance", Volume 1 Report and Recommendations of the National Bioethics Advisory Commission, Rockville, Md., August 1999). Specimens are stored as slides, paraffin blocks, formalin-fixed, tissue cultures, or extracted DNA. Research in fields such as cancer, infectious diseases, and mental disorders is advanced by quick access to such materials.

Biological samples are typically stored frozen, for example at about −20° C., −40° C., or at about −80° C. in cryotubes. Current industry methods of aliquotting samples involve thawing and refreezing the storage volume of the specimen each time an aliquot is removed. Laboratory results indicate that repeated freeze-thaw cycles degrade the specimen. However, freezing (cryostorage) extends the usable life of biological samples.

Further, current methods for accessing and processing samples involve delay and are a bottleneck in the use of these repositories. The sample is exposed to repeated freeze/thaw cycles that degrade the sample. Alternatively, storage of one specimen divided into multiple containers prior to freezing results in the inefficient use of freezer space and potential increased costs of cryotubes, labels, and time, and introduces a new source of error in processing.

An efficient method for obtaining samples (aliquots) from frozen biological specimen from storage volumes, i.e., reducing the need for excess freezer storage space, reducing lead-times for receiving specimens, and reducing degradation of specimens is needed.

SUMMARY

The invention in certain aspects provides an apparatus for obtaining a frozen sample from a frozen biological specimen, the apparatus includes: a drill for contacting the specimen within a container, wherein the drill includes a motor that actuates a hollow bit coring needle; and a grip for holding the specimen, in which the grip positions an open end of the container proximal to the needle, wherein the motor impels the needle into the specimen within the container, in which the frozen sample is removed from the specimen absent thawing of the specimen retained in the container.

In certain embodiments, the apparatus further includes a cooling reservoir to immerse a closed end of the container. It is envisioned that the cooling reservoir keeps the specimen frozen to avoid degradation; keeps the deposited sample frozen; prevents build-up of frost on the surface of the specimen; prevents addition of water to the specimen; and allows the operator to see the sample.

In a related embodiment of the apparatus the container is at least one selected from a cryotube, an array, a compartment in a molded recipient block, or a platform.

In certain embodiments of the apparatus, the motor provides a linear oscillatory motion. In alternative embodiments of the apparatus, the motor provides a rotary motion.

In another embodiment, the apparatus further includes a servo controller that communicates with a computer and is programmable with the computer and software. In an alternative embodiment, the apparatus is manually controlled.

In certain embodiments of the apparatus, the motor provides a force for the bit for striking the frozen specimen of about 30 to about 90 N, of about 35 to about 80 N, or of about 40 to about 75 N or the like, and compressive stresses of about 40 MPa to about 80 MPa, or of about 50 MPa to about 70 MPa or the like, and wherein the specimen is maintained at a temperature of about −90° C., or about −80° C., or about −70° C., or about −40° C. or about −20° C. or about −10° C., i.e., is a range of about −90° C. to about −10° C. or the like. Due to the cooling elements of the apparatus herein the buildup of frost on the specimen does not occur.

In a certain embodiment, the specimen has a volume of about 0.5 mL to about 5 mL, or of about 1.5 mL to about 15 mL, or of about 5 mL to about 50 mL or the like. In another embodiment, the sample has a volume of about 10 µl to about 50 µl or about 50 µl to about 100 µl or about 100 µl to about 500 µl or about 500 µl to about 1.0 mL.

In another embodiment of the apparatus, the drill bit needle further includes a distal tip having a ground point and lifting teeth. In certain embodiments of the apparatus the drill bit needle is ceramic or metal, for example, prefabricated standard surgical tubing including at least one metal selected from the group of, titanium, INCONEL 625, stainless steel 304, stainless steel 304L, stainless steel 316, and stainless steel 316L.

In another embodiment, the apparatus further includes a receiving device for the sample. In a related embodiment, the receiving device is a microarray, for example, the microarray is a recipient block having pre-molded cavities. The pre-molded cavities have a taper that enlarges the cavity towards the bottom of the cavity, for example, a taper to prevent the samples from falling out. In certain embodiments, the pre-molded cavities have a 2° taper or about a 5° taper, or about a 10° taper In certain embodiments, the apparatus further includes an ejection pin with a spring return or other type of automatic return, in which the ejection pin has a cross-sectional diameter less than and substantially similar to the inner diameter of the needle.

In another embodiment, the apparatus further includes a housing for at least one selected from the group of humidity control, refrigeration, operator safety from bloodborne pathogens, and sterility.

Another aspect of the invention herein is a method for obtaining a frozen sample from a frozen biological specimen and maintaining the specimen in a frozen condition, the method involving: contacting the specimen within a container with a drill having a motor that actuates a hollow bit coring needle; and a grip for holding the specimen, wherein the grip positions an open end of the container proximal to the needle, wherein actuating the motor impels the needle into the specimen; retracting the needle containing the frozen sample; and impelling the frozen sample from the needle to a receiving device, in which the frozen sample has been obtained from the frozen biological specimen and the specimen has been maintained in a frozen condition.

In another embodiment, the method further includes a cooling reservoir for immersing a closed end of the container. In a related embodiment the container is at least one selected from a cryotube, a compartment in an array, or a platform.

In certain embodiments, the method is performed in a local environment at a temperature of at least about −90° C. to about −10° C. or other temperatures that maintain the specimen in a frozen state. In another embodiment, the method further includes re-iterating the steps to obtain a duplicate aliquot of the sample. In a related embodiment, the method further includes re-iterating the steps to obtain a sample from at least one additional specimen.

In certain embodiments of the method, the motor that actuates a hollow bit drilling needle imparts a linear oscillatory motion to fracture the surface of the specimen.

In another embodiment of the method, impelling the frozen sample from the needle to a receiving device comprises actuating an ejection pin.

In another embodiment of the method, the receiving device is selected from the group consisting of an assay tube; a cryotube; a planar surface for pathology, histology and/or micro-array analysis; and a well of a multi-well dish.

BRIEF DESCRIPTION OF THE DRAWINGS

FIG. 4 panel A shows the cell line array. The prototype block includes 12 cavities. The tissue microarray contains 8 samples, 5 of tissue (light color) which are in the first two rows and 3 dyed OCT (Optimal Cutting Temperature) samples (dark color), which are in the third row. There were four empty cavities to show the shape of the cavity. Some of the samples are slightly darker because of the lightening. This is because they were ejected deeper into the molded holes. The molded holes have a 2° taper to prevent the samples from falling out. FIG. 4 panel B shows a stained sample. FIG. 4 panel C is a photomicrograph of cells from a sample stained with an antibody specific for the phosphorylated form of ERK.

FIG. 5 panel A is a photomicrograph of cells from a sample of frozen tumor glands (20×) showing specific membranous staining near the lumen of the cancer glands. FIG. 5 panel B is a photomicrograph of a control frozen large benign gland (20×) that is negative for specific staining showing weak non-specific staining in the stroma.

DETAILED DESCRIPTION

Figure 1:
FIG. 1 is a photograph showing a drill bit (TechnoDiamant) with an inside diameter (ID) of 0.0395 mm and an outside diameter (OD) of 0.070 mm. The tip includes a diamond/metal matrix.

The preservation and analysis of repositories of frozen biological specimens increases knowledge about diseases and provides a basis for developing better processes to prevent, diagnose, and treat these diseases.

Methods and apparatus provided herein use subsonic impact drilling into the still frozen specimens to extract sample (aliquots). The apparatus reduces the time required to obtain the samples by automating a process of extracting aliquot frozen samples, and requires less training and operation than current industry procedure. The apparatus and methods herein reduce lead time for laboratory researchers, speed medical research, and most important, provide for biological stability and integrity of the stored frozen specimens.

Industry Sample Processing

Biological repositories contain many frozen biological tissue and fluid specimens that are available to scientists to support research on biomarkers, nutrition, functional genomics, as well as other research areas. For example, blood banks collect approximately 15 million units of blood a year with 20,000 to 40,000 units stored for future use. Current biorepository facilities operate under prohibitively long lead times for delivery of ordered sample sets. For example, in the Nurses' Health Study (NHS) aliquotting operation, a research assistant processed 150 samples a week and a typical study consists of approximately 1000 samples. Therefore, it takes a research assistant more than six weeks in addition to another 1-2 weeks of data management to complete sample processing for a single study.

It is known that cycles of freeze-thawing result in the degradation of critical biological molecules such as RNA and proteins in the samples. This is troubling for researchers because the exact extent of degradation of the sample has not been quantified. Cryostorage is necessary to extend the usable life of biological specimens. To ensure that the highest quality samples reach the laboratories, repeated cycles of freeze-thawing must be minimized or eliminated.

One approach is characterized by storing samples in one container and aliquotting the required amount when requested. The sample is stored in a large cryotubes for example, a 1.8 mL or 4.5 mL cryotubes, and then is frozen. When a sample is requested the entire sample must be thawed, mixed, and requested aliquots are then removed. The remaining sample is refrozen in the original container. This method is an efficient use of labor, space, and energy because the sample is stored in one container. The drawback is the sample is exposed to many freeze/thaw cycles which degrade the sample and reduces its future value.

Another method of storage and sampling is storing the sample in aliquot sized containers. This method has the benefit of limited degradation, however it is an inefficient use of labor, freezer space and energy because many cryotubes need to be stored per sample. Further, there is added potential for confusion of identification of samples.

The third process of storing samples is a combination of the two previously presented methods. This hybrid method begins with mass frozen storage in, for example 1.8 mL or 4.5 mL cryotubes. After a request for analysis, a specimen is separated into, for example aliquots, and unused aliquots are then refrozen. This storage method of the specimens experience only two rounds of freeze-thawing. The utilization of freezer space is minimized until the specimen has been requested. This approach however compromises freezer space versus specimen quality, and may lead to confusion, and is labor intensive.

Introducing a frozen specimen aliquotting instrument to biological repositories will moderate the need for excess freezer storage space, reduce lead times for receiving specimen aliquots, minimize training needs, and limit degradation of specimens through reduction of repeated cycles of freeze-thawing. The proposed instrument directly samples the frozen specimen without the need for thawing. The required freezer space will be minimized because the specimen can be stored in larger volumes. The method of sampling or aliquotting through the automation of drilling frozen specimens introduces a significant improvement to the current sampling operations.

As used herein, the term "specimen" refer to stored frozen biological solid tissues and bodily fluids. The term "sample" and "aliquot" refer to portions of an initial specimen.

Design Objectives

A design is needed that will extract a one millimeter diameter core from a frozen biological specimen that will be maintained at or below about −90° C., −80° C., or −70° C., −40° C., or −20° C. Examples show that a frozen specimen exhibits the behavior of a brittle material. The manner in which the specimens are expected to fail and the various modes of heat generation are analyzed herein. Rotary coring methods were found in one preliminary test to be unsatisfactory because of high buckling and torsional stresses in the bit transmitted to the biological specimen.

An ultrasonic drilling system including piezoelectric stacks was compared to a subsonic system driven by a linear motor. The amount of heat generation was found to be directly proportional to frequency and stroke length, and the ultrasonic method was discounted as a potential solution through calculations and analysis.

Figure 3:
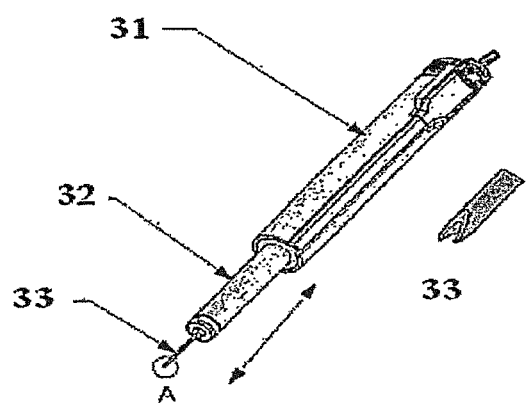
FIG. 3 is a diagram of a linear oscillating motor with drill bit, showing the driving system (31), slider (32), and bit (33).

A linear motor was then analyzed. An initial model tested was that designed by the LinMot Corporation and was chosen to provide the motion required of the design concept. Testing was performed with various bit geometries and an optimized, drill bit design was found. A sinusoidal, sonic motion at a frequency of 50 Hz and a 2 mm stroke was determined to provide the force necessary to initiate fracture within the sample. FIG. 3 shows a LinMot Linear motor with drilling bit.

The objective for the apparatus and methods provided herein is to obtain a sample from a frozen biological specimen. This objective presents a significant challenge resulting from the frozen specimen's fracture mechanics and the system's temperature constraints. Data from examples show that frozen saline is representative of the actual biological specimens and exhibit brittle characteristics. Through investigation, it was found that the brittle fracture mode results in formation of ice chips as a sample is then extracted. To assist in ice chip clearance, and allow for a deeper core an oscillatory motion was considered. Analysis of this type of apparatus determined that heat generation from friction was proportional to frequency and stroke length. Therefore objectives of further examples were to determine an oscillatory motion having low frequency and stroke, providing the force necessary to cause fracture within the sample. This motion is herein combined with a unique bit design to meet these objectives.

Design Parameters

Described parameters for the device include: volumetric uniformity maintained between aliquots; storage volumes utilized in an efficient matter, minimizing wasted sample; and minimal time and user input compared to prior art methods.

Described aliquot volume requirements based on laboratory testing criteria and industry efficiency requirements include at least about 10 μL, 50 μL, 100 μL, or about 500 μL for a successful analysis. In some cases, industry standards limit the aliquot volume to less than about 120 μL for efficient use of stored volumes. An exemplary cryotube holding 1.8 mL yields about 10 aliquots to meet industry efficiency standards. Peripheral damage to the surrounding specimen should be minimized to enable additional samples to be obtained from the same cryotube.

Sampling Methods

Rotary drilling using rotary motion to drive a drill bit into a material is shown in U.S. patent application number 2002/0129975 (Barth et al.). This ice auger system is in use for cutting and removing a solid core from frozen water, such as lakes and rivers. The purpose is to create a bore in the ice to remove a cylindrical ice core without significantly cracking the ice while reducing ice shavings. The system rotates by the use of a motor device connected to the upper end of the elongated shaft. The system cores with at least one bit for engaging the ice and uses flighting for continuous cutting. This system is not designed for precision obtaining a particular precise volume, or for maintaining the integrity of the inner core and surrounding ice. This system uses the basic rotary motion to cut and remove a solid core.

Ultra-subsonic corer/driller apparatus is shown in U.S. Pat. No. 6,689,087 (Pal et al.). This system produces a hammering action by use of ultra-subsonic and subsonic vibrations to produce effective drilling and coring. The ultra-subsonic driller and corer is used in planetary and geological exploration, military, and medical operations and is not designed for precision obtaining a particular precise volume, or for maintaining the integrity of the inner core and surrounding ice. This system uses the basic rotary motion to cut and remove a solid core.

Microarray technology suffers from disadvantages of smaller needles that buckle more easily due to the reduced diameter and provide less representation of a tissue specimen, e.g., a cancer biopsy. The sample sizes of about 3 mm to 4 mm in length, taken from a frozen donor block at about −20° C. can be obtained.

For some embodiments, diamond crystals are bonded under ultrahigh temperatures and pressures to cutting elements as shown in U.S. Pat. No. 5,437,343 (Cooley et al.). The thermally stable polycrystalline diamond cutting element is put to use on a rotary drag bit for drilling subterranean formations in a shearing motion. Boron nitride and silicon nitride are also super-hard materials and equally able to be bonded to cutting elements. The use of either sputter-coating diamonds or heat enameling super-hard materials onto the tips of the needle tip geometries will increase cycles to failure and maintain low initial contact stresses on the needle tip.

Bit Design

As used herein, the terms "bit", "drill bit", or "needle" refer to a hollow tube attached to a linear oscillatory motor for impacting and boring into a frozen biological specimen and removing a frozen sample.

The bit (needle) geometry is minimized to control radial cracking during drilling to allow for the maximum number of samples to be removed from each cryotube. Factors that effect radial crack propagation include impact velocity, impact force, bit surface area, and pitch of the first lifting tooth.

Reduction of stress exerted at the bit tip is an aspect and stresses on the bit are minimized to prevent bit failure from fatigue. This maximizes the number of cores possible per needle reducing operating costs and making the system more efficient.

To minimize binding of the needle as it penetrates the frozen sample, a frozen ice chip removal system is integrated into the design of the needle. This system facilitates removal of unwanted compacted frozen ice chips. Clearing the impact area of loose frozen ice chips reduces friction between the impact surfaces of the needle and the frozen sample.

Material selection for the needle is affected by factors including, strength, the ability to withstand temperature cycling between ambient and that of the frozen specimen, low cost, and ease of manufacturability.

Exemplary Model

A preliminary design for a frozen tissue microarrayer was based on a hollow drilling device (a diamond core drill bit from TechnoDiamant) that cuts by a combination of axial force and rotation. This combination of cutting modes reduces the stress levels in the needle compared to the use of axial force alone as is done in the existing commercially available equipment. The lower forces improve needle life and reduce the impact of coring on the architecture of the tissue. The needle seen in FIG. 1 was to cut 20 samples during the creation of a small frozen tissue array.

This drilling device is integrated into an x-y milling table, which offers computer control of x-y-z position and on/off control of the drill bit with fixed, but selectable, rotational speed. The milling table, or mini-mill, has 0.003175 mm step resolution with repeatability better than 0.0127 mm, which is more than adequate for this application. Samples were obtained with the Technodiamant needle and the mini-mill in frozen saline and tissue at −70° C.

Temperature Control

Frozen tissue specimens are held in tissue cassettes inserted in a holder and place in a coolant reservoir mounted on a milling machine. The coolant reservoir contains a dry ice-alcohol slurry to maintain the tissues in a frozen condition, and in certain embodiments includes an air coolant loop that provides a stream of cool air above the tissue block. This air circulation keeps the top of the block from warming and prevents buildup of frost on the block. This assembly was found suitable to maintain the block temperature at −70° C. or even colder, for at least eight hours.

The bit gains heat by friction as it moves within the frozen specimen and also by convection as it moves from the specimen to the recipient block. The bit is pre-cooled so that heat from friction is dissipated into the surrounding specimen. When used iteratively, the bit is pre-cooled in coolant before each use for example, the bit is contacted with a cold air stream above the specimen.

Figure 2:
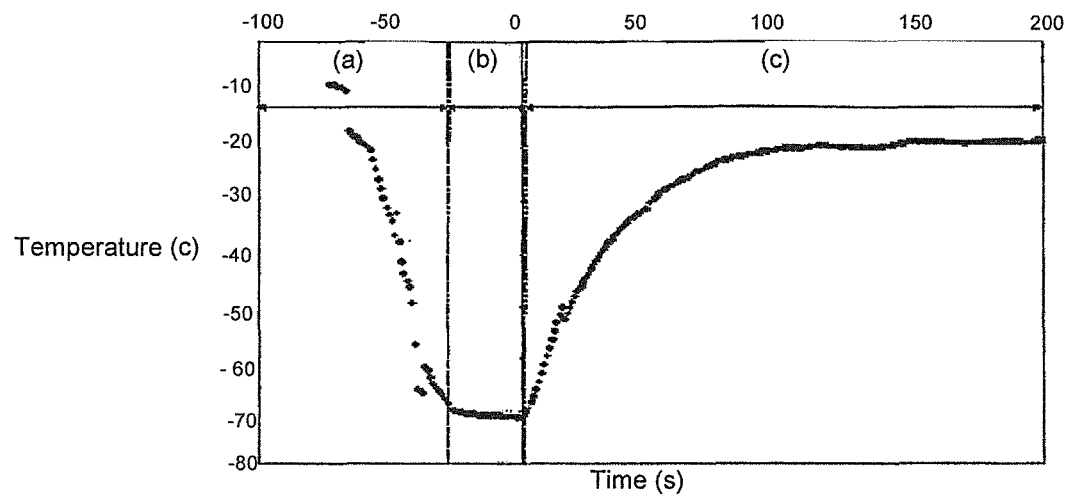
FIG. 2 is a plot of temperature of the sample in the hollow drill bit as a function of time. The method involved pre-cooling the bit using the coolant in the reservoir, establishing thermal equilibrium, and exposuring to air. The data are the average of four experiments.

To determine thermal properties of the system, a thermocouple treated with cryothermal grease to provide thermal contact was inserted into the bit which was chilled by contact with a dry ice/alcohol slurry. The bit was then moved out of the slurry and temperature recorded as shown in FIG. 2. The data show that the temperature of the sample was maintained at −20° C. for 100 s, sufficient to position and deposit the frozen sample in the recipient container.

Insertion of the Tissue Sample into the Recipient Block

The frozen sample is removed from the needle 33 with an ejection pin 39 (FIG. 6) having a very close fit to the inside diameter of the drilling needle to completely and cleanly remove the frozen sample from the needle. The pin further includes a spring return, and can include a Teflon seal to maximize sample recovery from the needle prior to iteration of the process. A tight fit between the Teflon piece at the distal end of the drilling needle and the inside diameter of the needle minimizes retention, and external material is removed using a cleaning station and the following steps: the drilling needle is inserted into a bed of brushes covered in a 10% bleach solution into which the coring needle is inserted. Once inserted the needle is moved around the bristles in an orbital motion while the needle is rotating and the ejection pin is moved up and down and the Teflon piece is partially exposed to allow its perimeter to be cleaned as well; in the next stage the method is similar to the herein except that the bleach is replaced by saline solution; then the station is dried to remove any residual saline solution; and a cooling station brings the needle to the desired temperature range.

Figure 6:
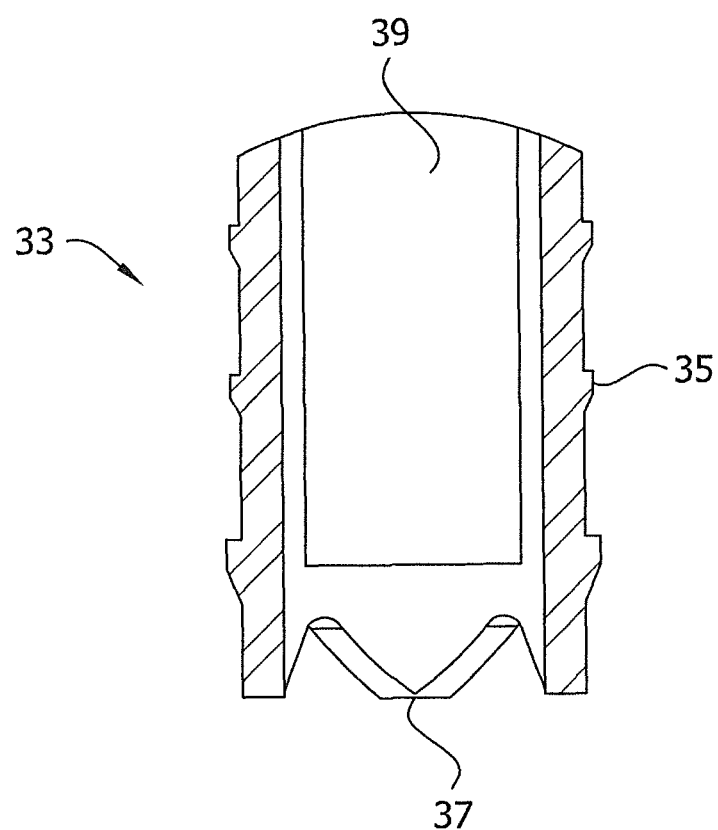
FIG. 6 is a cross section of an end of a coring bit needle having ground points and lifting teeth and an ejector pin for ejecting a frozen sample from the needle.
Figure 7:
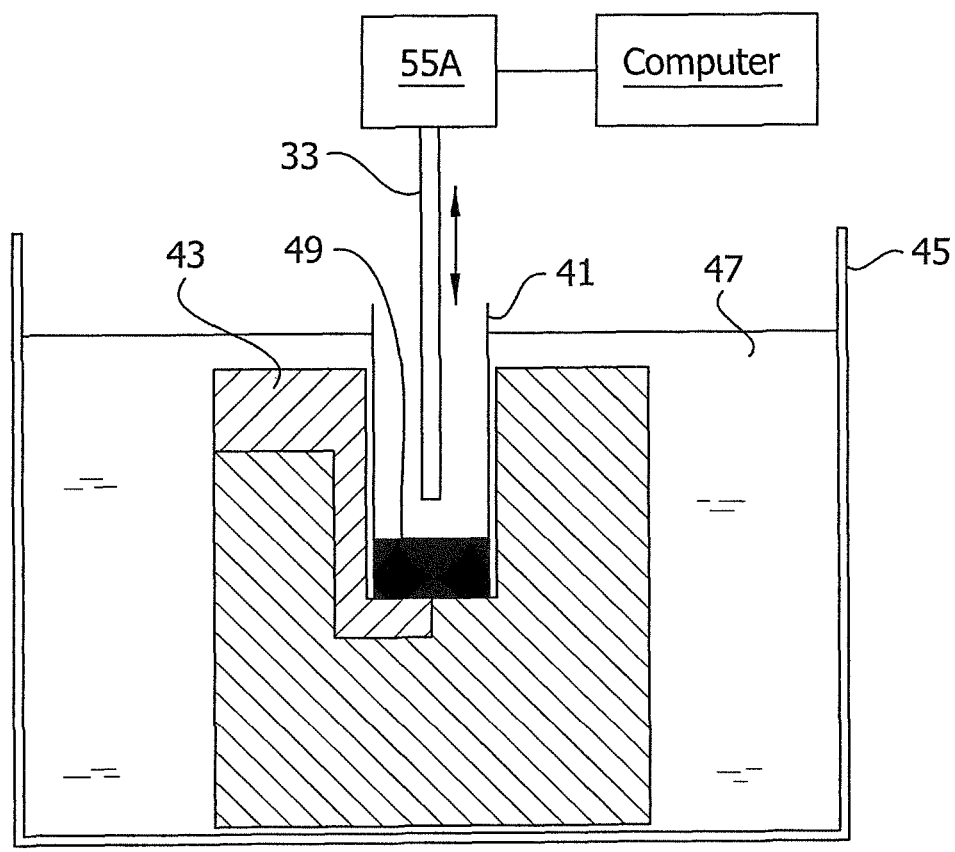
FIG. 7 is a schematic illustration of one embodiment of a system having a grip in the form of a block having premolded cavities for holding a container having a frozen specimen therein in a cooling reservoir while a servo motor produces linear oscillatory motion of the coring bit needle.
Figure 8:
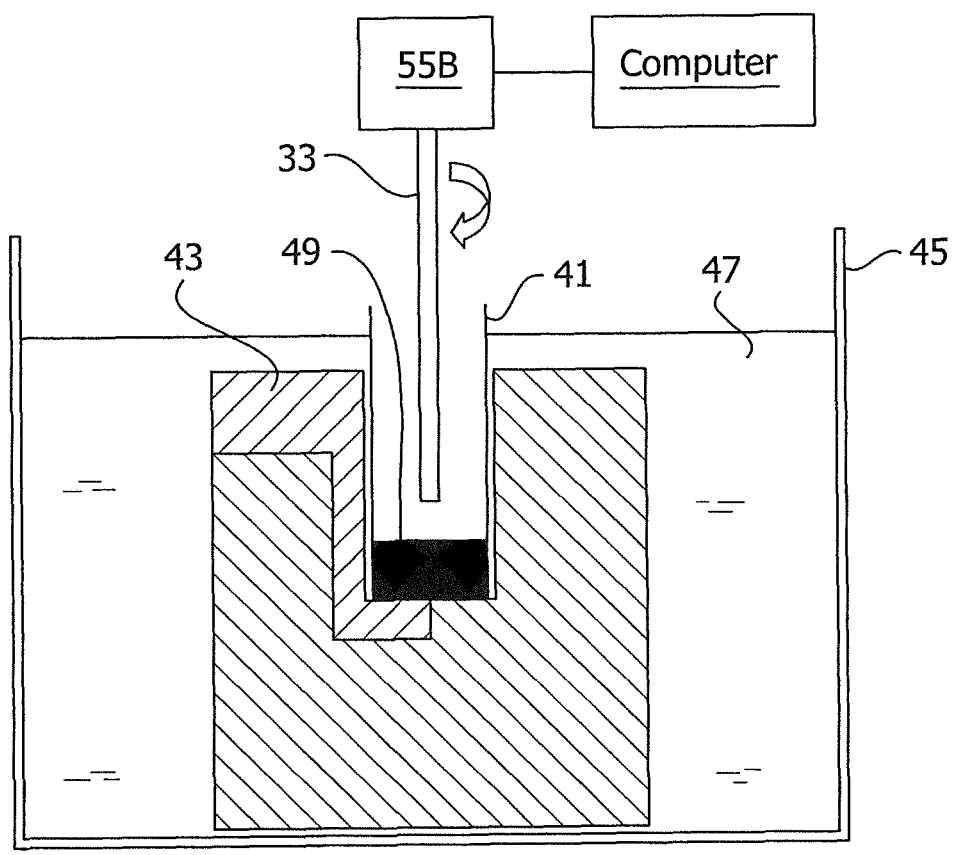
FIG. 8 is a schematic illustration of one embodiment of a system having a grip for holding a container having a frozen specimen therein in a cooling reservoir while a servo motor produces rotary motion of the coring bit needle.

As illustrated in FIGS. 6-8, the apparatus includes: a drill 33 contacting the specimen 49 within a container 41, wherein the drill includes a motor 55 that actuates a hollow bit coring needle 33; and a grip 43 for holding the specimen, in which the grip positions an open end of the container proximal to the needle, wherein the motor drives the needle into the specimen within the container, such that a frozen sample is removed from the specimen while the sample and the specimen are maintained in a frozen condition. The drill bit needle 33 includes a distal tip having a ground point 37 and lifting teeth 35, as illustrated in FIG. 6. FIG. 7 illustrates a system having a motor 55A that produces linear oscillating motion of the coring bit needle 33. FIG. 8 illustrates a system having a motor 55B that produces a rotary motion of the coring bit needle 33. The motors 55A, 55B in FIGS. 7 and 8 include a servo controller that communicates with a computer and is programmable with the computer and software, as illustrated. The apparatus in FIGS. 7 and 8 further includes a cooling reservoir 45 to immerse a closed end of the container 41. The systems illustrated in FIGS. 7 and 8 also include a cooling reservoir 45 for immersing a closed end of the container 41. As illustrated, the cooling reservoir 45 includes a coolant 47.

A cleaning assay was used as follows: ten samples of frozen human tissue taken as herein with the cleaning procedure and ten controls without the herein cleaning procedure were tested using the QuantiBlot® Human DNA Quantitation Kit (Applied Biosystems), a probe that is complementary to a primate-specific alpha satellite DNA sequence at the D17Z1 locus.

Tissue Cassette

The frozen tissue arrayer cassette for the frozen specimens machined from aluminum, for example, in one piece or in multiple pieces such that the cassette functions during freezing, storage, and subsequent array construction. Further, the same set can be used for the donor frozen specimen or for the recipient block.

Maintaining Tissue Morphology

In the process of obtaining samples from the frozen specimens and depositing these samples into the recipient block, the prior art methods apply unwanted forces to the cell and/or tissue. Drilling applies a shear force (rotation of the coring bit through the tissue) and a compression force (as the coring needle is pushed into the tissue). These coring forces have the potential to "twist" the tissue and compress the tissue. During insertion of the cores into the recipient block two forces are applied, one is a force from the ejector needle that is uniformly applied across the tissue surface and the other is a friction force at the intersection of the core with the inside diameter of the coring needle and the inside diameter of the cavity in the recipient block. These deposition forces have the potential to compress the tissue and cause relative motion between the perimeter and the center of the core.

An objective is to optimize the drilling and deposition forces to a point where there is no detectable alteration of the morphology of the tissue. The design variables under our control that impact on these forces include: the geometry of the drilling needle, the rotational speed during drilling, the rate at which the needle advances during drilling, the force applied and the rate at which the ejection pin pushes on the tissue, the difference between the outside diameter of the drill and the inside diameter of the cavity in the recipient block, the surface finish of the needle, and the accuracy with which the drilling needle is placed over the cavity in the recipient block. The positioning accuracy is under computer control, to preserve the biochemical fidelity of the tissue temperature maintained at −70° C.

Piezoelectric force and torque sensor (PCB Piezotronics, force: PCB 1102-05A and torque: PCB 2308-02A) installed in the arrayer measure the applied force and torque profiles (force and torque versus time) during the drilling process. The profiles are analyzed in conjunction with the pathology evaluation (see Examples herein) to identify the optimal design conditions. The metrics that are used to assess the merits of the variables include: morphology of the samples as a function of single tissue sections are evaluated to assess the impact of the drilling process. To perform the evaluation samples are taken from many different tissue types and sections are taken from both the donor tissues and the frozen tissue arrays and paired up. Double-blinded evaluations are performed by pathologists.

Sections from the donor tissues and the frozen arrays are cut and processed for the three key assays identified herein (IHC, FISH-DNA and -RNA) and a blinded evaluation are used. Immunohistochemistry (IHC)/Immunofluoreseence (IF) are techniques used to assess the presence of a specific protein or antigen in cells by use of a specific antibody, which binds to it, thereby allowing visualization and examination under a microscope. The advantage of IF over IHC is that many different fluorescent chromagens are available and thus different antigens can be differentially labeled and visualized at the same time.

(Fluorescence) in-situ hybridization are techniques that allow specific DNA/RNA sequences (e.g. genes) to be detected by use of labeled complementary DNA/RNA probes in morphologically preserved chromosomes, cells or tissue sections. This provides microscopic topological information to gene activity at the DNA, or mRNA level. Likewise herein, the advantage of FISH over ISH is that many different fluorochromes are available and thus different DNA/RNA sequences can be differentially labeled and visualized at the same time.

The invention having been fully described, it is further shown by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Example 1

Determination of Required Force

A general objective is minimization of heat generation occurring as a result of this process. Experimental simulations with frozen saline analysis determined that the force necessary to create fracture in a sample maintained at about −90° C., at about −80° C., or at about −70° C. could range between about 30 N and 90N, specifically 43-72 N with an intended hit design. This range arises from observed variation in fracture toughness of experimentally frozen sample, based on observed data.

Several design alternatives were investigated, including drills having motion that is rotary or linear oscillatory.

Example 2

Rotary Drill

The rotary motion method of coring is accomplished by driving a coring bit with a rotary motion (i.e. drill press). This method requires both high axial and torsional loading of the core bit to penetrate the sample. Attempts at rotary drilling of frozen biological specimens showed some limited success, generating few successful samples as determined by analytical data. Additional data from analysis of the linear oscillatory motion are shown herein.

Example 3

Linear Oscillatory Motion

A linear oscillatory ultrasonic drilling system provided herein includes a piezoelectric stack, which drives a horn to a resonant frequency. Typical ultrasonic systems operate at frequencies above 20 KHz with displacements up to 30 μm. Examples herein of sampling using a commercial ultrasonic polisher found excessive amount of heat, confirmed by computation. The ultrasonic polishing device was equipped with a drilling bit and introduced into the frozen sample. The device completely melted the frozen specimen. The adjustability and control over the parameters of motion is also limited.

Therefore, another example of a type of linearly oscillating system investigated herein was a digitally controlled linear motor system. This type of motor can be used to drive a system at subsonic speeds and provide the motion profile required. An exemplary motor of this type suitable for the methods herein is manufactured by the LinMot Corporation (Delevan, Wis. 53115), and provides a tubular linear motor using a cylindrical stator to drive a hollow slider containing neodymium magnets. An advantage of this motor is added control over the parameters of motion.

Example 4

Exemplary Apparatus

A linear motor, for example from LinMot Corporation, produces a sonic, linear oscillatory motion for sampling. The stator and slider assembly is operated by a servo controller which communicates and is programmed through the COM port of any PC equipped with the provided software. Analytical investigations were performed to determine optimized conformance to the objectives.

Initial calculations were used to determine the amount of heat generated in the system. Possible modes of heat generation in the system include: fracture, friction, and comminution. A negligible amount of heat is generated from fracture because of the brittle nature of the material. Heat from friction was calculated to be directly proportional to the frequency and stroke of the motion. Calculations showed that the ultrasonic method of coring produces 27 times more heat from friction than the LinMot system. Comminution arises from the mechanical size reduction of the sample particles, which will occur as the bit cores into the frozen sample. The heat from comminution is calculated using the Rittenger Equation, in which energy methods are used to relate initial and final chip surface areas to an amount of heat generation. As the Rittenger method was developed empirically, it is difficult to quantify heat generated from comminution in this system. In addition to heat generation, heat transfer from chip transport was calculated with the known boundary conditions of the system, including size of the chips and velocity of chip flow. As with heat generated from comminution, transfer of heat from chip flow is optimally determined through testing.

The critical force necessary to initiate fracture at −79° C. was determined by the following equation.

$$\text{Critical force} = P = [K_{1C}/A] * [HV/E]^{1/2} * C_0^{1.5}$$

This relates the fracture toughness, Vickers hardness, and an assumed resultant radial crack length of the material, to determine the critical force to cause fracture.

Due to a range of fracture toughness values for ice, a range of the necessary force was determined to be between 43 N and 72 N. To support this, finite element analysis using ANSYS was computed. The lower limit of 43N from the above critical force calculation was applied to an infinite sheet of ice and the resulting principle stresses were computed. This ANSYS analysis produced compressive stresses of 60 MPa. Empirical observations of ice fracturing under uni-axial compression show a necessary stress of 4-30 MPa. This value is less than the 60 MPa resulting from the 43 N force. The combination of the critical force calculation and ANSYS analysis, indicated suitability of a LinMot driven system.

Example 5

Free Fall Force

A free-fall force approach was conducted as an additional means of determining the force necessary to fracture frozen saline. Using the work-energy theorem and conservation of energy, it was calculated that the experiment imparted 73 N of force to the frozen saline. Fracture occurred and ice chips were produced, with an indentation that was approximately twice the diameter of the bit. This test provided further verification of the theoretical analysis.

It was concluded that an advantage of the LinMot driven design concept is control over motion, achieved through the manipulation of the system's software. The LinMot system is exemplary for oscillatory motion with minimal heat generation. In addition, the LinMot is equipped with a hollow slider design that allows for removal of the frozen sample after it is obtained.

Example 6

Improvements and Equivalents

A servo memory for the LinMot or equivalent systems is upgraded to allow for more data points. The LinMot controller runs a motion profile that contains 4000 data points. An increase in data points enables the system to operate over a larger range of frequency, amplitude, and force while also providing a feed rate.

Other beneficial improvements are use of titanium as the bit material to increase the hardness of the bit by 45%. Additional modifications to the bit geometry allow the bit to remove chips from the sample while obtaining a sample.

Another improvement is to place a hydrophobic coating on the bit, such as Teflon. This reduces friction and allows easier sample recovery from the bit.

Example 7

Bit Impact Test

Using the LinMot subsonic impact driller, the system was mounted in a stationary position such that the slider of the LinMot was the only moving part. LinMot software includes force feedback of the amperage and driving force levels of the systems.

Several single impact analyses were conducted to determine the pressure required to fracture the ice surface with minimal radial cracking. The test set-up included several operations at various average speeds ranging from 1.22 to 240 mm/s. A 30° conical stud needle made of 316 stainless steel was threaded into the LinMot slider. To measure the increase in pressure on the surface of the ice, the tip of the stud needle was ground down to a flat surface to increase the surface area in contact with the ice at impact.

To determine the impact velocity the average velocity of the last three data points immediately preceding impact with the ice were considered. The average impact velocity was found to be 128 mm/s. The driving force at the point of contact was determined by using a conversion factor from the software and amperage spike in the output. The amperage at the surface of the ice was found to be 1.47 A. The driving force was determined to be 29.48 N. The mass of the slider was also taken into consideration as a contributor to the impact energy through momentum. The mass of the slider is 0.5 kg. The momentum was calculated to be 0.064 kg*m/s, using the driving force and mass of the slider. The calculated impact time was 0.006 seconds. The impact force and pressure of the system was determined by dividing the momentum by the impact time length.

The highest inertial forces are generated near the surface of the ice when the slider is extended to the furthest extent from the stator. The optimum ice surface fracture profile was at 120 mm/s. The maximum impact area was determined through testing to be 2.374 mm² and resulted in impact force of 40.153 N, a resultant pressure of 10 MPa.

Example 8

Bit Analysis

A factorial design of experiments was performed to determine how critical factors of the bit geometry affected the stress in the bit during impact as shown in Table 1 herein. Six independent factors were chosen. A: outer diameter, B: impact angle, C: fillet radius, D: tooth height, E: impact width, and F: tooth angle.

A fractional 2k factorial design experiment was used. For each factor a high-level and low-level dimension was indicated. This resulted in 64 combinations that were reduced using the half fraction of the full factorial design based on six factors. The 32 combinations were analyzed in ANSYS to solve for maximum Von Mises stress.

TABLE 1

Combination maximum stress results showing the high-low combinations and the results.

|  | A | B | C | D | E | F | Max Stress (Mpa) |
|---|---|---|---|---|---|---|---|
| 1 | −1 | −1 | −1 | −1 | −1 | −1 | 321.30 |
| 2 | −1 | −1 | −1 | −1 | 1 | 1 | 106.70 |
| 3 | −1 | −1 | −1 | 1 | −1 | 1 | 345.60 |
| 4 | −1 | −1 | −1 | 1 | 1 | −1 | 118.47 |
| 5 | −1 | −1 | 1 | −1 | −1 | 1 | 371.00 |
| 6 | −1 | −1 | 1 | −1 | 1 | −1 | 123.60 |
| 7 | −1 | −1 | 1 | 1 | −1 | −1 | 451.80 |
| 8 | −1 | −1 | 1 | 1 | 1 | 1 | 132.50 |
| 9 | −1 | 1 | −1 | −1 | −1 | 1 | 692.00 |
| 10 | −1 | 1 | −1 | −1 | 1 | −1 | 209.00 |
| 11 | −1 | 1 | −1 | 1 | −1 | −1 | 1,731.00 |
| 12 | −1 | 1 | −1 | 1 | 1 | 1 | 363.82 |
| 13 | −1 | 1 | 1 | −1 | −1 | −1 | 935.38 |
| 14 | −1 | 1 | 1 | −1 | 1 | 1 | 255.52 |
| 15 | −1 | 1 | 1 | 1 | −1 | 1 | 4,034.00 |
| 16 | −1 | 1 | 1 | 1 | 1 | −1 | 521.39 |
| 17 | 1 | −1 | −1 | −1 | −1 | 1 | 321.16 |
| 18 | 1 | −1 | −1 | −1 | 1 | −1 | 116.03 |
| 19 | 1 | −1 | −1 | 1 | −1 | −1 | 379.33 |
| 20 | 1 | −1 | −1 | 1 | 1 | 1 | 115.63 |
| 21 | 1 | −1 | 1 | −1 | −1 | −1 | 403.87 |
| 22 | 1 | −1 | 1 | −1 | 1 | 1 | 119.31 |
| 23 | 1 | −1 | 1 | 1 | −1 | 1 | 415.38 |
| 24 | 1 | −1 | 1 | 1 | 1 | −1 | 144.62 |
| 25 | 1 | 1 | −1 | −1 | −1 | −1 | 755.18 |
| 26 | 1 | 1 | −1 | −1 | 1 | 1 | 198.71 |
| 27 | 1 | 1 | −1 | 1 | −1 | 1 | 1,641.00 |
| 28 | 1 | 1 | −1 | 1 | 1 | −1 | 328.76 |
| 29 | 1 | 1 | 1 | −1 | −1 | 1 | 925.27 |
| 30 | 1 | 1 | 1 | −1 | 1 | −1 | 247.16 |
| 31 | 1 | 1 | 1 | 1 | −1 | −1 | 3,478.00 |
| 32 | 1 | 1 | 1 | 1 | 1 | 1 | 542.18 |

TABLE 2

Combination maximum stress results

|  | Outer Diameter | Impact Angle | Fillet Radius | Tooth Height | Impact Width | Tooth Angle |
|---|---|---|---|---|---|---|
| Avg of High | 681.40 | 1,128.45 | 888.66 | 1,004.70 | 227.63 | 714.27 |
| Average Low | 238.59 | 202.96 | 215.35 | 206.61 | 423.45 | 240.04 |
| Main Effects | 442.82 | 925.49 | 673.31 | 798.09 | −195.82 | 474.23 |

TABLE 2-continued

Combination maximum stress results

| Outer Diameter | Impact Angle | Fillet Radius | Tooth Height | Impact Width | Tooth Angle |
|---|---|---|---|---|---|

The main effects of these six factors were calculated using the results shown in Table 2. For example the main effect of the outer diameter was calculated by subtracting the average stress of the combinations, where that factor is a high value, from the average stress of the combinations where that factor is a low value. Table 2 shows the results of these calculations, wherein the numerical results are the average stress expressed in MPa.

The outer diameter and the impact angle were found not to have much effect on the stress output. Stress decreases as the impact width is increased. The remaining factors show an increase in stress as the dimension of the factor is increased. Of these factors, the tooth angle shows the greatest effect. The tooth height has less of an influence than the tooth angle and more than the fillet radius. These results along with maximum surface area to break ice during impact were used to optimize the bit geometry.

Example 9

Manufacturability and Material Selection

Drilling bit designs were analyzed and were optimized for ease of manufacturability by utilizing available standard tubing sizes, adjusting tolerance levels, and designing the bits with common dimensions.

Bit designs were developed to compare thick wall and thin wall designs. These designs vary in only two or three dimensions. Consistent measurements allow for ease of manufacturing by limiting set up time. Variation between the bits is limited to dimensions that affect the performance of the device. Testing determines the features that are better suited to the application.

The bit is made of prefabricated standard surgical tubing. Available materials include titanium, INCONEL 625, and each of the stainless steel 304, 304L, 316, 316L. Table 3 shows the material properties of four materials at room temperature. The drilling bit utilized in this application will be subject to low temperatures. The 300 series of austenitic stainless steels (characterized by high ductility, low yield stress and high tensile strength) are important because they retain a large portion of their room temperature toughness at temperatures as low as −252° C.

TABLE 3

Material properties of stainless steels

| Stainless Steel Materials | Modulus of Elasticity [Gpa] | Yield Strength [MPa] | Endurance Limit [MPa] | Brinell Hardness [HB] |
|---|---|---|---|---|
| 304 | 200 | 205 | 259 | 201 |
| 316 | 200 | 205 | 259 | 217 |
| 304L | 200 | 170 | 244 | 201 |
| 316L | 200 | 170 | 244 | 217 |

The material properties in Table 3 show that stainless steel 316 is an optimal material. Stainless steels 304 and 316 have the largest yield strength and endurance limit. The 316 stainless steels are harder materials, for the use herein is advantageous. The 316 stainless steel has optimal values and is widely used in the biomedical industry. Further, the 316 steel is more resistant to general corrosion then the 304 stainless steels. Common tube sizes are commercially available from a variety of sources including N.E. Small Tube (Litchfiled, N.H.), MicroGroup (Medway, Mass.), Unimed (Solvay, Brooklyn, N.Y.), and Popper and Sons (New Hyde Park, N.Y.).

The bit design includes a tip geometry that meets several criteria, including maximizing crack propagation axially into the frozen specimen while minimizing the propagation in the radial direction; bit life; and optimizing material characteristics, including diamond coating options and other additions as is beneficial to requirements.

Example 10

Bit Design

A main objective is to obtain a sample equivalent of 110 μL (100 mm$^3$)±10 of a specimen. Using a standard 60 mm in length cryotube, the diameter required for the drilling function of the needle is approximately 1.9 mm, calculated as shown herein using the volume of the needle cylinder. The length of frozen material available in a 60 mm cryotube is approximately 35 mm.

$$V_{CYL} = \pi r^2 L$$

$$r = \sqrt{\frac{100 \text{ mm}^3}{\pi * 35 \text{ mm}}}$$

$r = .954$ mm $D = 1.908$ mm $V_{CYL}$ = Coring Volume = 100 mm$^3$ $r$ = Inner Radius of Needle (mm)

$D$ = Inner Diameter of Needle (mm)

A bit used for initial testing included a four inch long needle connected to an unthreaded brass slug with a flat diamond coated tip. The needle was made from 303 stainless steel tubing with an inner diameter (ID) of 1.0668 mm and an outer diameter (OD) of 1.9812 mm. This design was found to have long cyclic loading life of the bit, and uniformity of crack length propagation at impact due to the circular nature of the impact surface. However this flat impact face was found to be inefficient in producing successful samples with a model system, frozen saline solution.

A further bit design utilized the same ID and OD as herein, with a threaded brass slug pressed onto the needle to facilitate attachment, and a tip ground down to a 75° point. This dual tip design showed improved performance compared to the design herein in ease of use and length of the obtained frozen sample of approximately 15.875 mm.

Improvements to the dual tip design included the following: reducing stress in the bit so to achieve longer bit life, improving the cutting effectiveness of the system to shorten sampling time, and incorporating an ice chip removal system to clear unwanted frozen chips from the impact area to prevent binding of the needle. The embodiment herein further addresses these issues.

Example 11

Exemplary Drilling Bit

An exemplary drilling bit was used that includes a wall with a 2.5 mm OD and a 1.80 mm ID, 90° cuts yielding 4 tips which do not come to infinitesimal points but rather have flat impact surfaces of approximately 0.3 mm thickness. This feature reduces the maximum stress in the bit upon impact. Additionally, 0.25 mm fillets at the cuts were found further to reduce stress.

Lifting and ejection of the frozen sample model of saline is facilitated through the use of lifting teeth spaced at 1 mm intervals herein the impact surface along the entire length of the bit. To make contact with the frozen sample a lifting tooth having a diameter of 2.7 mm was made, which is a 0.1 mm larger diameter than the remaining lifting teeth. This modification was made to create a buffer zone below which no cleared ice chips may re-enter and cause the binding of the needle. The air gap between the cylinder wall of frozen sample and the smaller lifting teeth function to assist in the removal of ice chips through air vortices created by the oscillatory Z-axis motion of the needle. The height of the first lifting tooth was changed to 0.1 mm in order to eliminate the large deflection seen at the lifting tooth, ice interface in observed stress analyses. The angles between the lifting teeth and the needle cylinder wall are at 22° in order to provide a steep slope for an easier transition of the ice particles between the lifting teeth and frozen sample cylinder wall.

Stress analyses were conducted on the quad tip design to validate selection of the particular geometry. As dual tip design exhibited a maximum von Mises stress of 1978 MPa and a maximum deflection of 0.254 millimeters, when the maximum stress required to fracture frozen saline solution in tri-axial compression of 60 MPa was loaded as a pressure force onto the contact faces of the bit. The maximum stress experienced by the needle equated to 179.281 cycles to failure for the bit. Using the average time to extract a core of 150 seconds at 60 Hz this equates to 9000 cycles per core and roughly 20 cores to failure. This analysis was reproduced with the prototype design to determine the improvements in cyclic loading.

To accurately simulate an initial impact test, a pressure of 345 MPa (see Table 3 herein) was added as a structural load to all the impact faces of the contact bit. This load simulates an upper bound for the forces that will act on the needle tip. This pressure was calculated by taking the maximum force the LinMot can apply to the system, 120 Newtons, and applying it to the surface areas of initial contact.

TABLE 3

Impact analysis pressure load calculation

| | |
|---|---|
| P = F/A | P = Pressure (Mpa) |
| P = 30 N/.0869 mm$^2$ | F = Force (Newtons) |
| P = 345 N/mm$^2$ (Mpa) | A = Area (mm$^2$) |

The bit model was constrained at the top in the X, Y, and Z axes as well as rotations in all the axes to accurately simulate the physical constraints that are applied to the needle by the LinMot system.

This design generates a maximum von Mises stress of 354 MPa, a reduction of 82% over the previous dual tip design. The largest deflection in the model is 0.0026 mm, a reduction of 99% over the previous needle design. As is evident, the maximum stress occurs above the impact faces of the bit.

Example 12

Fatigue Life

The maximum Von Mises stress seen in this bit was used to determine a lower bound for the number of cycles to failure, $N_f$, of the needle. The maximum stress for the previous needle was equivalent to 179,281 cycles to failure for the bit. Using the average time to obtain a sample of 150 seconds at 60 Hz this equates to 9000 cycles per sample and 19.92 cores to failure. Analysis yielded a maximum stress of 354 MPa. The bit experiences stress solely in compression and not in tension, therefore the alternating stress is half of the maximum stress. Utilizing the alternating bit stress the Basquin Equation was employed to determine the cycles to failure of the bit.

Test results show that the $N_f$ of the hit yields 2,003,197 cycles to failure of the bit. At 7500 cycles per sample for the design (50 Hz at 150 seconds per sample) this is equivalent to 267 samples before failure of the bit occurs, an improvement of 1335% over the previous design.

Example 13

Automation

An embodiment of the method and apparatus herein includes controlling Z-axis motion through an actuator and MCS. A load cell is incorporated to gather force measurements near the point of impact. The control system include an MCS capable of operating both actuators and processing the output from the load cell.

Force data during the drilling operation provides information about the friction force along the core shaft. Data gathered allows adjusting the bit geometry based on maximum impact force measurements. The load cell must withstand vibrations of 50 Hz as this is the operating frequency of the LinMot actuator. It must also take force measurements at a rate of speed greater than 200 Hz in order to provide sufficient information about the impact event. The maximum force that can be generated by the system is 120 N of force, combined with the momentum energy of the slider and the coring bit. Minimal deformation under loading will assist in isolating impact deflection from deflection of the load cell.

Actuation of the LinMot is controlled primarily through the embedded controller in the amplifier. This controller is calibrated to calculate output currents based on the mass of the slider and the input motion profile. The added mass of the load cell and the drilling bit is not accounted for when the controller calculates a move. Therefore, every move will now have an amount of reactionary motion due to the extra inertia the controller is not expecting. The oscillating mass increases by approximately 113.

Deflection of the load cell is minimized to enable measurement of small scale changes in the waveform. The load cell should not deflect during loading to maximize the energy transmitted to the frozen sample. Preliminary investigation of impact characteristics indicates that impact depth, the distance into the ice the bit travels each impact, is about 0.04 mm. This translates to a gross motion velocity of 2 mm/s. The low distance helps to minimize radial ice fracture by reducing crack propagation length in all directions.

The apparatus is programmed to oscillate a 2 mm amplitude sine wave at a frequency of 50 Hz. The frequency response of the load cell is higher than the frequency of the drilling operation to allow for proper measurements. To characterize impact dynamics, force data is gathered at least 4 times a cycle. The sample frequency is greater than 200 Hz. The acquisition instrument must also be considered at this point in time.

During initial testing, LabView is utilized to process the data from the load cell in order to allow the team to characterize coring operations. However any load cell suitable for use with LabView is suitable for use with other control systems. Many load cell manufacturers offer devices within the design specifications for example a piezoelectric load cell from PCB Piezotronics (Depew, N.Y.) for this application due to the short lead-time and the qualifications of the quartz force sensor. Piezoelectric load cells are based on the electromechanical response of certain crystals to dynamic loading. Force measurements are made by observing the variation of supply voltage to a crystal while it is dynamically loaded. The crystal, quartz in this case, exhibits varying conductivity, which is measured as a change in the supply voltage at the power supply. This variation is then converted into an analog DC voltage output. Commercially available load cells such as the PCB are available in a range of types and the power supplies to go with them. System integration, on the electric side, involves plugging the amplifier output into LabView. The apparatus then has capability to monitor force during impact and adjust the coring profiles appropriately. The PCB 221B02 quartz force sensor is suitable for the design requirements herein.

The linear actuator is rigidly connected to the supporting structure, oriented vertically. The exemplary LinMot is rigidly connected to the mounting plate. The application of force is approximately 50 mm distance from the front surface of the mounts. An approximation of the maximum forces possible during coring yields an axial force of 300 N and a moment of 15 Nm across the carriage. There is negligible moment around the axis and negligible force in the x- or y-axis.

A fully integrated automated system embodiment having a force feedback sensor is tested. The LinMot subsonic impact driller is set at a frequency of 50 Hz. The incorporation of a force sensor provides useful feedback on areas of high stress within the ice and assist in determining the optimal motion profile.

Quantification of a fully automated system versus a manually operated system involves trial tests of the needle bit having the design described herein. Using the LinMot impact driller at the determined 50 Hz profile, and as a variable in the testing procedure, a break of between the 0.05 mm steps controlled by the Z-axis was performed, as shown in Table 5 herein.

TABLE 5

Motion profile testing

| Step Size [mm] | Break [s] | Frequency [Hz] | Drill Depth [mm] | Results |
|---|---|---|---|---|
| 0.05 | 0.2 | 50 | 16.7 | bound up |
| 0.05 | 0.3 | 50 | 14.8 | bound up |
| 0.05 | 0.4 | 50 | 21.4 | bound up |
| 0.05 | 0.5 | 50 | 25.3 | successful |

A change in the break of the Z-axis motion controller concluded in a successful core to a depth of 25.3 mm. Another test increased the step of the Z-axis to increase the rate of drilling and constrain the frequency of the LinMot to 50 Hz and the break of the Z-axis to 0.5 seconds, with results shown in Table 6 herein.

TABLE 6

Time efficiency increases in drilling

| Step Size [mm] | Break [s] | Frequency [Hz] | Drill Depth [mm] | Results |
|---|---|---|---|---|
| 0.1 | 0.5 | 50 | 25.0 | successful |
| 0.15 | 0.5 | 50 | 25.0 | successful |
| 0.2 | 0.5 | 50 | 24.3 | successful |
| 0.25 | 0.5 | 50 | 24.9 | successful |
| 0.3 | 0.5 | 50 | 25.3 | successful |
| 0.35 | 0.5 | 50 | 25.0 | successful |
| 0.4 | 0.5 | 50 | 24.7 | successful |

The conclusion of these tests and time efficiency provided an optimal motion profile.

The automated system of the needle drilling is an improved tool for aliquotting of frozen biological specimens. The drilling bit geometry was optimized through virtual design and by experiment testing. The results were factored to yield the main effects of each feature with relation to maximum stress in the coring bit. Results showed that impact width and tooth angle were most important in effecting the stress in the bit during impact. These results drove optimizing bit for fatigue life by reducing stress while maintaining required impact area to break ice. The optimized prototype bit exceeds the satisfactory usable lifespan of 150 samples Example 14

Tissue Microarrays (TMA) from Frozen Specimens

TMAs (tissue microarrays) have been used throughout the world for several years. The benefit of placing hundreds of tissue core samples in one block now has proven time and again to be invaluable in the research of large study cohorts. The H&E (Hematoxylin and Eosin) stained slide prepared on one TMA block has been used to reveal diagnostic information for hundreds of patient cases. Additionally the TMA is gaining popularity for use in areas beyond clinical research. For example, in analysis of genes, antibodies and proteins in a large cohort of for example, 3,000 patients, the TMA is a method of reviewing multiple tissue types and diagnostic features from the saline preparation. Conversely, staining 3,000 individual slides to review only one particular antibody is not only antiquated, but prohibitive in terms of labor cost in technical time and for reagents. The TMA has earned a significant place in the research environment and is useful in the clinical field as this method fulfills the need for high throughput and accuracy in the clinical laboratory grows.

While the present methods of TMA involve paraffin embedded tissue, there are drawbacks to handling fixed tissue in paraffin. While most techniques in the past were designed for fixed tissue now we are seeing an increased need for frozen tissue to be used in the place of fixed material. In order for a tissue to be embedded in paraffin, it has to go through a process of fixation and processing as well as clearing and infiltration at high temperatures in liquid paraffin. These processes have the effects of decreasing the antigenicity of the tissue as well as cross linking the proteins and degrading other tissue structures, with the negative outcome that many studies can not be done on the fixed specimen. Pathology analysis has long become attuned to the architecture of the formalin fixed specimen and problems that lie therein. However, there is a need for fresh frozen tissue microarrays (ffTMAs) in order to perform studies for many of the more labile antigens, proteins, DNA, RNA, mRNA, peptides to name just a few.

The optimal specimen in the pathology laboratory is the snap frozen fresh tissue specimen, which is stored in the −80° C. freezer. This specimen may be used for any investigational process at any time. The frozen sample remains in a state of biological functionality and is ready for investigational use, after days, months, or years from freezing. Frozen sections may be cut with the use of a cryostat to obtain a diagnostic section to evaluate the entire surface of the specimen, or for special studies for DNA and RNA extraction, or for FISH and ISH immunofluorescent techniques. Individually sectioned slides may be fixed for specific procedures resulting in optimal test results and less time removing undesired effects of improper fixation. Smaller amounts of this precious tissue are required for sectioning thereby saving the remaining specimen for future work. Ultimately, a small portion of the fresh frozen specimen may be fixed and processed for a permanent pathological record, thus, allowing for the fixed tissue to be used in paraffin TMA in years to come.

The versatility and breadth of techniques available makes the fresh frozen specimen the most valuable to the research and diagnostic laboratory. Most general pathology laboratories and especially those in academic centers snap freeze a portion of fresh tissue samples when possible. These tissues are of special interest due to the specific diagnosis. Examples of such specimens are lymph nodes, prostate tumors, breast tumors, nerve and muscle.

There are large repositories of tumors and fresh frozen specimens located in academic centers for both diagnostic and research purposes. However, there is a need for consistency of specimen handling in order to maintain diagnostic integrity of the tissue for valid interpretative results.

Cell line arrays have been constructed herein and frozen cell line arrays were experimentally shown to be suitable for determining protein phosphorylation in frozen samples. Protein Phosphorylation is an important and useful mechanism to demonstrate however, the results are very unreliable in formalin fixed samples.

A multi tumor array was constructed that included samples of tissues from sources such as prostate cancer benign prostate, colon, renal carcinoma, liver, and lung. The process of constructing the array yielded a ffTMA frozen tissue microarray for which the results of the final product yielded beneficial data, for example, a test for Hepsin imaging peptides which would have been otherwise impossible to obtain with fixed tissue. Protein antigens are often destroyed during fixation or require strong antigen retrieval.

Referring to the construction of the frozen multi tumor array, arrays were created herein using preserved in the −80 freezer tissues. Results are equivalent between fresh frozen tissue and those frozen more than two years previously showing the most valuable points of frozen tissue.

The multi tumor array was constructed using the manual Beecher MTA 1 arrayer and OCT compound (Optimal Cutting Temperature, from TissueTek), a water soluble embedding medium, used as the embedding medium and is the medium used for maintaining the specimens in the frozen state, which helps to avoid desiccation in the −80 freezer. In order to keep the area around the arrayer cold enough to maintain a temperature suitable to the integrity of the tissue, dry ice was used in and around the arrayer. The tissue samples as well as the array were monitored for temperature fluctuations as to ensure temperature control. The array was prepared similarly to a paraffin array, in that a mapping and file were maintained of all specimens and locations. Samples were removed from the donor frozen specimen blocks and were placed in to a recipient embedding well. The array enabled experiments with this frozen multi tumor array that would be impossible by any prior art technology, treating an entire selection of tissues at one time on one slide with Hepsin imaging peptides. By prior techniques, many sections of individual tissues would have been required to analyze the value of various tissue types and the potential for example controls.

The frozen samples are sectioned on a research quality cryostat (Leica Microsystems, Heidelberg, Germany). After each section is cut it is then picked up with the use of the CryoJane Tape Transfer System (Instrumedics Inc., Hackensack, N.J.). The tape transfer system allows for the secure adherence of the tissue to the slide, which is also provided by Instrumedics. There is a greater yield of samples per slide and much less waste of tissue samples using the CryoJane system and slides.

Frozen Cell Line Arrays

Protein phosphorylation is an important mechanism for cellular signaling. Current methods for determining phosphorylated proteins often yield unreliable results. Intracellular phosphatases and formalin-fixation dephosphorylate these proteins within milliseconds of ischemia which occurs when cells or tissue are harvested. The addition of phosphatase inhibitors does not seem to not stop this process. One method to preserve the phosphorylation status is to harvest tissue or cell lines, add phosphatase inhibitors and immediately decrease the temperature by placing the sample on ice and freezing it.

Figure 4:
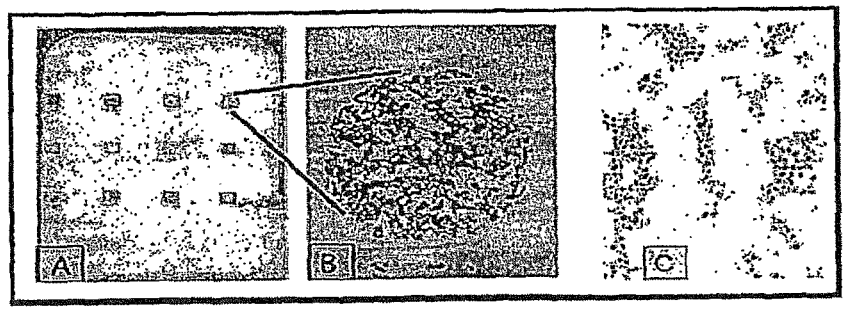
FIG. 4 is a photograph showing a frozen cell line array made using a mold for frozen tissue arraying of samples obtained by the methods herein.

To generate the frozen cell line arrays 30 μl of a cell line suspension in phosphate-buffered saline is transferred with a 20 μl pipette tip into the wells of the mold (panel A in FIG. 4). Currently, we are able to array up to 16 separate cell line samples at once. Panel B in FIG. 4 depicts a core of this array with an H&E staining. Since cell lines consist of one single cell clone obtaining a solid tissue core is not necessary. In panel C of FIG. 4, a high magnification of a cell line core stained with an antibody specific for the phosphorylated form of the extracellular-regulated kinase (ERK) is shown. Strong nuclear staining can be appreciated.

Multi-Tumor Frozen Tissue Array

Monitoring expression of Hepsin, that is a biomarker overexpressed in prostate cancer, would be extremely useful in the diagnosis of prostate cancer. Although PSA is being currently used in standard screening tests for prostate cancer, it is not always a good indicator. Hence there is a need for developing a non-invasive method for the diagnosis of prostate cancers. Hence Hepsin-specific peptides have been identified for in vivo imaging.

Peptides binding to Hepsin were identified by phage display technology. The binding of these peptides to Hepsin was confirmed using cell lines that over-express Hepsin. However, in order to develop an imaging agent, it is important to demonstrate that the peptides are capable of binding to the protein antigen in human tissues. The major obstacle to testing the peptides on patient tissue samples or tissue microarrays (TMA) is that these peptides are confirmation specific and require an intact antigen for optimal binding. The TMAs constructed using formalin fixed paraffin embedded (FFPE) tissues cannot be used for testing such peptides since protein antigens are often destroyed during the process of fixation and antigen retrieval. Although most antigens retain a conformation that can be recognized by large antibodies for routine immuno histochemistry (IHC), the antigens that are peptides are smaller molecules, and require an intact local conformation. Hence such studies require frozen material as local conformations are well preserved in frozen tissues.

Figure 5:
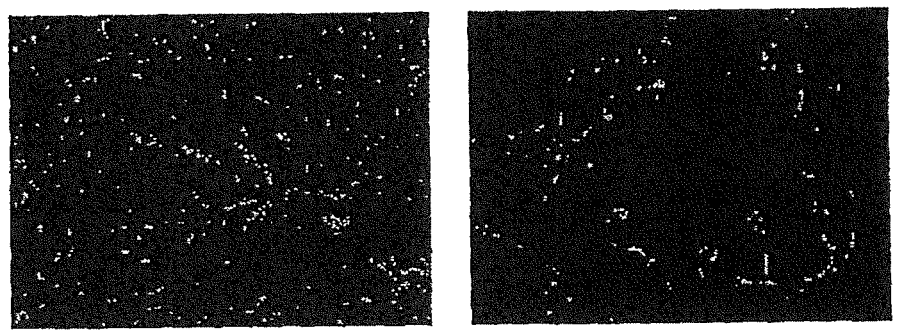
FIG. 5 is a photograph of frozen tissue microarray (TMA) stained with FITC-labeled Hepsin peptide.

In order to test candidate Hepsin binding peptides for in vivo imaging, a frozen multi-tumor TMA consisting of tumor material from prostate, lung, colon, liver, renal, breast and benign prostate tissue constructed manually at our lab was used. FIG. 5 shows specific staining of Hepsin using the FITC-labeled peptides in cancer glands. Specific membranous staining of Hepsin can be seen in the luminal side of the cancer glands which is markedly absent in the benign gland.

Hence, data herein show successful test potential for Hepsin imaging peptides using a frozen TMA. The multi-tumor frozen array constructed for this study also offers a potential to test markers in diverse tissues for imaging of different types of cancers.

What is claimed is:

1. An apparatus for obtaining frozen samples from frozen biological specimens that are contained within containers, the apparatus comprising:
    a coring bit for obtaining the frozen samples from the frozen biological specimens;
    a positioning system adapted to position the coring bit and containers relative to one another for sampling of the specimens by the coring bit while the specimens remain in their respective containers;
    a motor that is adapted to drive the coring bit into the specimens within the containers to obtain the frozen samples and withdraw the coring bit and the frozen samples contained therein from the containers;
    an ejection system adapted to eject the frozen samples from the coring bit; and
    a cooling station adapted to pre-cool the coring bit to ensure the coring bit is cooled to a desired temperature range before the coring bit contacts the specimens.

2. The apparatus of claim 1 wherein the cooling station is adapted to pre-cool the coring bit to a temperature low enough that the temperatures of the samples are kept at or below about −20C until the samples are ejected from the coring bit.

3. The apparatus of claim 1 wherein the cooling station is adapted to pre-cool the coring bit to a temperature low enough that the temperatures of the frozen samples are kept at or below about −70C until the samples are ejected from the coring bit.

4. The apparatus of claim 1 wherein the cooling station is adapted to pre-cool the coring bit to a temperature that is less than about −70C.

5. The apparatus of claim 1 wherein the coring bit has a wall that is less than about 1 mm in thickness.

6. The apparatus of claim 1 wherein the cooling station is adapted to contact the coring bit with a cooling medium and wait until an equilibrium temperature is achieved.

7. The apparatus of claim 1 further comprising a cooling system for keeping the biological specimens in the containers frozen, the cooling system including a coolant reservoir for containing a coolant, wherein the cooling station is adapted to pre-cool the coring bit by contacting the coring bit and the coolant with one another.

8. The apparatus of claim 1 wherein the cooling station is adapted to contact the coring bit with a stream of coolant above the biological specimens.

9. The apparatus of claim 1 wherein the coring bit is coated with a coating that reduces friction.

10. The apparatus of claim 1 wherein the motor is adapted to produce rotary motion of the coring bit.

11. The apparatus of claim 1 wherein the motor is adapted to produce linear oscillatory motion of the coring bit.

12. The apparatus of claim 1 further comprising a cleaning station adapted for cleaning the coring bit.

13. A method for obtaining frozen samples from frozen biological specimens, the method comprising:
    (a) cooling a coring bit for obtaining a frozen sample from one of the frozen biological specimens to a desired temperature range at a cooling station, the desired temperature range having an upper end that is no more than about −20C;

(b) inserting the cooled coring bit into the frozen biological specimen to obtain a frozen sample retained in the coring bit and then withdrawing the coring bit from the frozen biological specimen; and, (c) repeating steps (a)-(b) to obtain another frozen sample from another frozen biological specimen.

14. The method of claim 13 further comprising:

moving the coring bit and the frozen sample retained therein from the frozen biological specimen to a position for receiving the frozen sample; and ejecting the frozen sample from the coring bit at said position.

15. The method of claim 13 wherein cooling the coring bit further comprises cooling the coring bit to a temperature low enough to keep the frozen samples in the coring bit at or below about −20C until they are ejected from the coring bit.

16. The method of claim 13 wherein cooling the coring bit further comprises cooling the coring bit to a temperature low enough to keep the frozen samples in the coring bit at or below about −70C until they are ejected from the coring bit.

17. The method of claim 13 wherein cooling the coring bit comprises cooling the coring bit to a temperature that is less than about −70C.

18. The method of claim 13 wherein cooling the coring bit comprises contacting the coring bit with a cooling medium and waiting until an equilibrium temperature is achieved.

19. The method of claim 13 further comprising using a coolant to keep the biological specimens frozen, wherein cooling the coring bit comprises contacting the coring bit and the coolant with one another.

20. The method of claim 13 wherein cooling the coring bit comprises contacting the coring bit with a stream of coolant above the biological specimens.

21. The method of claim 13 wherein the coring bit is coated with a coating that reduces friction.

22. The method of claim 13 wherein inserting the coring bit into the frozen biological specimen comprises rotating the coring bit.

23. The method of claim 13 wherein inserting the coring bit into the frozen biological specimen comprises producing linear oscillatory motion of the coring bit.

24. The method of claim 13 further comprising cleaning the coring bit at a cleaning station.

* * * * *